(12) United States Patent
Bieringer et al.

(10) Patent No.: US 7,056,863 B1
(45) Date of Patent: Jun. 6, 2006

(54) SYNERGISTIC HERBICIDAL COMPOSITIONS HERBICIDES FROM THE GROUP OF THE HYDROXYPHENYLPYRUVATE DIOXYGENASE INHIBITORS

(75) Inventors: Hermann Bieringer, Eppstein (DE); Andreas van Almsick, Oberursel (DE); Erwin Hacker, Hochheim (DE); Lothar Willms, Hofheim (DE)

(73) Assignee: Aventis CropScience GmbH, Frankfurt am Main (DE)

( * ) Notice: Subject to any disclaimer, the term of this patent is extended or adjusted under 35 U.S.C. 154(b) by 530 days.

(21) Appl. No.: 09/691,915

(22) Filed: Oct. 19, 2000

(30) Foreign Application Priority Data

Oct. 22, 1999 (DE) ................................ 199 50 943

(51) Int. Cl.
*A01N 47/36* (2006.01)
*A01N 35/06* (2006.01)
*A01N 41/10* (2006.01)

(52) U.S. Cl. ..................... 504/136; 504/136; 504/215; 504/350

(58) Field of Classification Search ................ 504/136, 504/138, 215, 350
See application file for complete search history.

(56) References Cited

U.S. PATENT DOCUMENTS

| | | | | |
|---|---|---|---|---|
| 5,416,061 A | 5/1995 | Hewett et al. | ............... | 504/141 |
| 5,650,375 A | 7/1997 | Hacker et al. | ............... | 504/136 |
| 5,801,121 A | 9/1998 | Kamano et al. | ............ | 504/288 |
| 5,912,207 A | 6/1999 | Scher et al. | ................ | 504/190 |
| 6,004,903 A | 12/1999 | von Deyn et al. | .......... | 504/239 |
| 6,046,134 A * | 4/2000 | De Gennaro et al. | ....... | 504/133 |
| 6,239,070 B1 * | 5/2001 | Luff | ............................ | 504/105 |
| 6,376,429 B1 * | 4/2002 | Van Almsick et al. | ...... | 504/271 |

FOREIGN PATENT DOCUMENTS

| | | |
|---|---|---|
| EP | 0 230 596 | 8/1987 |
| EP | 0 354 047 | 2/1990 |
| EP | 0 768 033 | 4/1997 |
| EP | 0 807 382 | 11/1997 |
| EP | 0 810 227 A1 | 12/1997 |
| FR | 2 675 340 | 10/1992 |
| JP | 4-230301 * | 8/1992 |
| WO | WO 95/15691 | 6/1995 |
| WO | WO 95/28839 | 11/1995 |
| WO | WO 96/26200 | 8/1996 |
| WO | WO 97/22253 | 6/1997 |
| WO | WO 97/23134 | 7/1997 |
| WO | WO 97/23135 | 7/1997 |
| WO | WO 97/34486 | 9/1997 |
| WO | WO 97/48276 | 12/1997 |
| WO | WO 98/29406 | 7/1998 |
| WO | WO 98/56251 | 12/1998 |
| WO | WO 99/65314 | 12/1999 |
| WO | WO 99/66795 | 12/1999 |
| WO | WO 00/00029 | 1/2000 |
| WO | WO 00/00031 | 1/2000 |
| WO | WO 00/03591 | 1/2000 |
| WO | WO 00/08936 | 2/2000 |
| WO | WO 00/14087 | 3/2000 |
| WO | WO 00/30447 | 6/2000 |

OTHER PUBLICATIONS

Database WPI, Section Ch, Week 199733, also referred to as XP 002162798, 1997.
Lee et al, "The Structure-Activity Relationships of the Triketone Class of HPPD Herbicides", Dec. 1998, pp. 377–384, Pesticide Science, vol. 54.
Database Accession No. 126.196420 CA, Jun. 25, 1996, also referred to as XP-002171352, Abstract of ZA 9510980.
Patent Abstracts of Japan, JP 05070426, vol. 017, No. 391, published Mar. 23, 1993.
Datbase WPI, Section CH, Week 199240, also referred to as XP-002171353, Abstract of JP4230301.
Database WPI, Section CH, Week 199833, also referred to as XP-002171354, Abstract of JP62-063503.
Database WPI, Section CH, Week 199833, also referred to as XP-002171354, Abstract of JP10-529841.

\* cited by examiner

*Primary Examiner*—S. Mark Clardy
(74) *Attorney, Agent, or Firm*—Frommer Lawrence & Haug LLP

(57) ABSTRACT

Herbicidal compositions comprising
A) at least one compound from the group of the hydroxyphenylpyruvate dioxygenase inhibitors and
B) at least one compound from the group
B-a) herbicides which are selectively active in cereals against monocotyledonous and/or dicotyledonous harmful plants,
B-b) herbicides which are selectively active in corn against monocotyledonous and/or dicotyledonous harmful plants,
B-c) herbicides which are selectively active in rice against monocotyledonous and/or dicotyledonous harmful plants,
B-d) herbicides which are nonselectively active in land which is not under cultivation and/or selectively active in transgenic crops against monocotyledonous and/or dicotyledonous harmful plants
are described.

The activity of these compositions is superior to that of the herbicides applied on their own.

1 Claim, No Drawings

US 7,056,863 B1

SYNERGISTIC HERBICIDAL COMPOSITIONS HERBICIDES FROM THE GROUP OF THE HYDROXYPHENYLPYRUVATE DIOXYGENASE INHIBITORS

The invention is in the field of crop protection compositions which can be used against undesirable vegetation and which comprise, as active compounds, a combination of at least two herbicides.

More specifically, the invention relates to herbicidal compositions which, as active compound, comprise a herbicide from the group of the hydroxyphenylpyruvate dioxygenase inhibitors in combination with at least one further herbicide.

Herbicides from the abovementioned group of the hydroxyphenylpyruvate dioxygenase inhibitors are known from numerous documents. Recently disclosed inhibitors of this type usually carry a substituted benzoyl radical on a likewise substituted radical from the group consisting of cyclohexanedione, pyrazole, isoxazole, isothiazole and 3-oxopropionitrile. Thus, WO 97/23135 describes benzoylpyrazoles, EP-A 0 810 227 describes benzoylisoxazoles and WO 98/29406 describes benzoylcyclohexanediones having in each case herbicidal action. Further herbicidal benzoyl derivatives are known from WO 00/14087. This document also indicates the mechanism of action, which is the same as for the benzoyl derivatives described in the present invention.

In practice, however, the use of the benzoyl derivatives known from these publications has frequently been associated with disadvantages. Thus, the herbicidal activity of the known compounds is not always satisfactory, or, in the case of satisfactory herbicidal activity, undesirable damage to the useful plants is observed.

The activity of herbicides depends inter alia on the type of herbicide used, its application rate, the preparation, the harmful plants to be controlled in each case, climatic and soil conditions, etc. A further criterion is the persistency or the rate at which the herbicide is degraded. Changes in the sensitivity of harmful plants to an active compound which may occur on prolonged use or in specific geographical areas may also have to be taken into account. Such changes manifest themselves by a more or less pronounced loss in activity and can only be compensated under certain conditions by higher herbicide application rates.

Owing to the large number of possible influencing factors, there is virtually no individual active compound which has all the desired properties for different requirements, in particular with respect to the species of harmful plant and the climatic zones. Furthermore, there is the permanent object to achieve the desired effect using more and more reduced herbicide application rates. A lower application rate reduces not only the amount of active compound required for the application, but generally also reduces the amount of formulation auxiliaries required. Both reduce the economical expense and improve the ecological compatibility of the herbicide treatment.

A frequently used method for improving the use profile of a herbicide is the combination of the active compound with one or more other active compounds which contribute the desired additional properties. However, the combined use of a plurality of active compounds is frequently associated with phenomena of physical and biological incompatibility, for example insufficient stability of a joint formulation, decomposition of an active compound or antagonism of the active compounds. What is desired are, in contrast, active compound combinations having a favorable activity profile, high stability and, if possible, synergistically enhanced activity, thus permitting the application rate to be reduced, compared with the individual application of the active compounds to be combined.

None of the publications mentioned further above discloses that numerous compounds from the group of the hydroxyphenylpyruvate dioxygenase inhibitors show synergistic effects when combined with selected other herbicides.

It is an object of the present invention to provide herbicidal compositions having better properties than those of the prior art.

The invention provides herbicidal compositions, comprising an effective amount of A) at least one compound of formula (I) and its agriculturally customary salts (Component A)

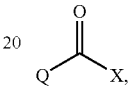

in which
X is a radical $X^1$, $X^2$ or $X^3$

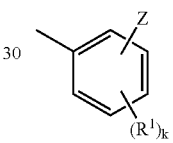

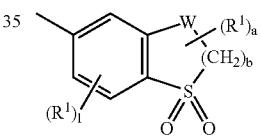

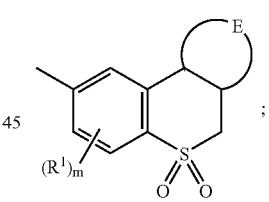

Q is a radical $Q^1$, $Q^2$, $Q^3$, $Q^4$ or $Q^5$

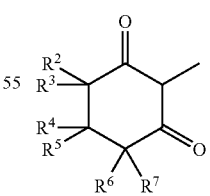

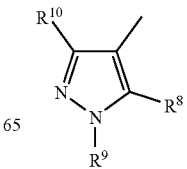

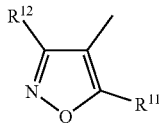

(Q³)

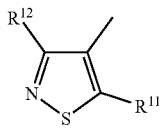

(Q⁴)

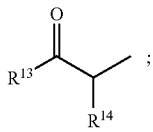

(Q⁵)

Z is a radical Z¹, CH₂—Z¹ or Z²;

Z¹ is a five- to ten-membered monocyclic or bicyclic saturated, partially saturated, fully unsaturated or aromatic ring which is attached via carbon or nitrogen and which, in addition to carbon atoms, contains 1, 2, 3 or 4 heteroatoms from the group consisting of oxygen, sulfur and nitrogen and which is unsubstituted or mono- or polysubstituted by halogen, cyano, nitro, cyano-($C_1$–$C_4$)-alkyl, CO—R¹⁵, ($C_1$–$C_4$)-alkyl, halo-($C_1$–$C_4$)-alkyl, ($C_3$–$C_8$)-cycloalkyl, ($C_1$–$C_4$)-alkoxy, halo-($C_1$–$C_4$)-alkoxy, ($C_1$–$C_4$)-alkylthio, halo-($C_1$–$C_4$)-alkylthio, di-($C_1$–$C_4$)-alkylamino, by phenyl which is optionally mono- or polysubstituted by halogen, cyano, nitro, ($C_1$–$C_4$)-alkyl or halo-($C_1$–$C_4$)-alkyl or by an oxo group;

Z² is ($C_3$–$C_{12}$)-cycloalkyloxy-($C_1$–$C_4$)-alkyl, aryloxy-($C_1$–$C_4$)-alkyl, heteroaryloxy($C_1$–$C_4$)-alkyl, heterocyclyl-($C_1$–$C_4$)-alkyl, halo-($C_1$–$C_4$)-alkoxy-($C_1$–$C_4$)-alkyl, aryl-($C_1$–$C_4$)-alkoxy-($C_1$–$C_4$)-alkyl, heteroaryl-($C_1$–$C_4$)-alkoxy-($C_1$–$C_4$)-alkyl, heterocyclyl-($C_1$–$C_4$)-alkoxy-($C_1$–$C_4$)-alkyl, aryl-($C_3$–$C_8$)-cycloalkylthio-($C_1$–$C_4$) alkyl, heteroaryl-($C_3$–$C_8$)-cycloalkylthio-($C_1$–$C_4$)-alkyl, heterocyclyl-($C_3$–$C_8$)cycloalkylthio-($C_1$–$C_4$)-alkyl, ($C_3$–$C_8$)-cycloalkylsulfinyl-($C_1$–$C_4$)-alkyl, ($C_3$–$C_8$)cycloalkylsulfonyl-($C_1$–$C_4$)-alkyl, ($C_3$–$C_8$)-cycloalkylamino-($C_1$–$C_4$)-alkyl, ($C_3$–$C_8$)-cycloalkylsulfonyloxy-($C_1$–$C_4$)-alkyl, ($C_3$–$C_8$)-cycloalkylsulfonylamino ($C_1$–$C_4$)-alkyl, ($C_3$–$C_8$)-cycloalkylcarbonyl-($C_1$–$C_4$)-alkyl, ($C_3$–$C_8$)cycloalkylcarbonyloxy-($C_1$–$C_4$)-alkyl, ($C_3$–$C_8$)-cycloalkoxycarbonyl-($C_1$–$C_4$)-alkyl, ($C_3$–$C_8$)-cycloalkylcarbonylamino-($C_1$–$C_4$)-alkyl, ($C_3$–$C_8$)cycloalkylaminocarbonyl-($C_1$–$C_4$)-alkyl, ($C_4$–$C_{12}$)-cycloalkyl-($C_1$–$C_4$)-alkyl, ($C_4$–$C_{12}$)-cycloalkylthio-($C_1$–$C_4$)-alkyl, ($C_4$–$C_{12}$)-cycloalkylsulfinyl-($C_1$–$C_4$)-alkyl, ($C_4$–$C_{12}$)-cycloalkylsulfonyl-($C_1$–$C_4$)-alkyl, ($C_4$–$C_{12}$)-cycloalkylamino-($C_1$–$C_4$)-alkyl, ($C_4$–$C_{12}$)-cycloalkylsulfonyloxy-($C_1$–$C_4$)-alkyl, ($C_4$–$C_{12}$)-cycloalkylsulfonylamino-($C_1$–$C_4$)-alkyl, ($C_4$–$C_{12}$)-cycloalkylcarbonyl-($C_1$–$C_4$)-alkyl, ($C_4$–$C_{12}$)-cycloalkylcarbonyloxy-($C_1$–$C_4$)-alkyl, ($C_4$–$C_{12}$)-cycloalkoxycarbonyl-($C_1$–$C_4$)-alkyl, ($C_4$–$C_{12}$)-cycloalkylcarbonylamino-($C_1$–$C_4$)-alkyl, ($C_4$–$C_{12}$)cycloalkylaminocarbonyl-($C_1$–$C_4$)-alkyl, arylthio-($C_1$–$C_4$)-alkyl, arylsulfinyl($C_1$–$C_4$)-alkyl, arylsulfonyl-($C_1$–$C_4$)-alkyl, arylamino-($C_1$–$C_4$)-alkyl, arylsulfonyloxy-($C_1$–$C_4$)-alkyl, arylsulfonylamino-($C_1$–$C_4$)-alkyl, arylcarbonyl-($C_1$–$C_4$)-alkyl, arylcarbonyloxy-($C_1$–$C_4$)-alkyl, aryloxycarbonyl-($C_1$–$C_4$)-alkyl, arylcarbonylamino-($C_1$–$C_4$)-alkyl, arylaminocarbonyl-($C_1$–$C_4$)-alkyl, heteroarylthio-($C_1$–$C_4$)-alkyl, heteroarylsulfinyl-($C_1$–$C_4$)-alkyl, heteroarylsulfonyl-($C_1$–$C_4$)-alkyl, heteroarylamino-($C_1$–$C_4$)-alkyl, heteroarylsulfonyloxy-($C_1$–$C_4$)-alkyl, heteroarylsulfonylamino-($C_1$–$C_4$)-alkyl, heteroarylcarbonyl-($C_1$–$C_4$)-alkyl, heteroarylcarbonyloxy-($C_1$–$C_4$)-alkyl, heteroaryloxycarbonyl-($C_1$–$C_4$)-alkyl, heteroarylcarbonylamino-($C_1$–$C_4$)-alkyl, heteroarylaminocarbonyl-($C_1$–$C_4$)-alkyl, heterocyclylthio-($C_1$–$C_4$)-alkyl, heterocyclylsulfinyl-($C_1$–$C_4$)-alkyl, heterocyclylsulfonyl-($C_1$–$C_4$)-alkyl, heterocyclylamino-($C_1$–$C_4$)-alkyl, heterocyclylsulfonyloxy-($C_1$–$C_4$)-alkyl, heterocyclylsulfonylamino-($C_1$–$C_4$)-alkyl, heterocyclylcarbonyl-($C_1$–$C_4$)-alkyl, heterocyclylcarbonyloxy-($C_1$–$C_4$)-alkyl, heterocyclyloxycarbonyl-($C_1$–$C_4$)-alkyl, heterocyclylcarbonylamino-($C_1$–$C_4$)-alkyl, heterocyclylaminocarbonyl-($C_1$–$C_4$)-alkyl, halo-($C_1$–$C_4$)-alkylthio-($C_1$–$C_4$)-alkyl, halo-($C_1$–$C_4$)-alkylsulfinyl-($C_1$–$C_4$)-alkyl, halo-($C_1$–$C_4$)-alkylsulfonyl-($C_1$–$C_4$)-alkyl, halo-($C_1$–$C_4$)-alkylamino-($C_1$–$C_4$)-alkyl, halo-($C_1$–$C_4$)-alkylsulfonyloxy-($C_1$–$C_4$)-alkyl, halo-($C_1$–$C_4$)-alkylsulfonylamino-($C_1$–$C_4$)-alkyl, halo-($C_1$–$C_4$)-alkylcarbonyl-($C_1$–$C_4$)-alkyl, halo-($C_1$–$C_4$)-alkylcarbonyloxy-($C_1$–$C_4$)-alkyl, halo-($C_1$–$C_4$)-alkyloxycarbonyl-($C_1$–$C_4$)-alkyl, halo-($C_1$–$C_4$)-alkylcarbonylamino-($C_1$–$C_4$)-alkyl, halo-($C_1$–$C_4$)-alkylaminocarbonyl-($C_1$–$C_4$)-alkyl, aryl-($C_1$–$C_4$)-alkylthio-($C_1$–$C_4$)-alkyl, aryl-($C_1$–$C_4$)-alkylsulfinyl-($C_1$–$C_4$)-alkyl, aryl-($C_1$–$C_4$)-alkylsulfonyl-($C_1$–$C_4$)-alkyl, aryl-($C_1$–$C_4$)-alkylamino-($C_1$–$C_4$)-alkyl, aryl-($C_1$–$C_4$)-alkylsulfonyloxy-($C_1$–$C_4$)-alkyl, aryl-($C_1$–$C_4$)-alkylsulfonylamino-($C_1$–$C_4$)-alkyl, aryl-($C_1$–$C_4$)-alkylcarbonyl-($C_1$–$C_4$)-alkyl, aryl-($C_1$–$C_4$)-alkylcarbonyloxy-($C_1$–$C_4$)-alkyl, aryl-($C_1$–$C_4$)-alkyloxycarbonyl-($C_1$–$C_4$)-alkyl, aryl-($C_1$–$C_4$)-alkylcarbonylamino-($C_1$–$C_4$)-alkyl, aryl-($C_1$–$C_4$)-alkylaminocarbonyl-($C_1$–$C_4$)-alkyl, heteroaryl-($C_1$–$C_4$)-alkylthio-($C_1$–$C_4$)-alkyl, heteroaryl-($C_1$–$C_4$)-alkylsulfinyl-($C_1$–$C_4$)-alkyl, heteroaryl-($C_1$–$C_4$)-alkylsulfonyl-($C_1$–$C_4$)-alkyl, heteroaryl-($C_1$–$C_4$)-alkylamino-($C_1$–$C_4$)-alkyl, heteroaryl-($C_1$–$C_4$)-alkylsulfonyloxy-($C_1$–$C_4$)-alkyl, heteroaryl-($C_1$–$C_4$)-alkylsulfonylamino-($C_1$–$C_4$)-alkyl, heteroaryl-($C_1$–$C_4$)-alkylcarbonyl-($C_1$–$C_4$)-alkyl, heteroaryl-($C_1$–$C_4$)-alkylcarbonyloxy-($C_1$–$C_4$)-alkyl, heteroaryl-($C_1$–$C_4$)-alkoxycarbonyl-($C_1$–$C_4$)-alkyl, heteroaryl-($C_1$–$C_4$)-alkylcarbonylamino-($C_1$–$C_4$)-alkyl, heteroaryl-($C_1$–$C_4$)-alkylaminocarbonyl-($C_1$–$C_4$)-alkyl, heterocyclyl-($C_1$–$C_4$)-alkylthio-($C_1$–$C_4$)-alkyl, heterocyclyl-($C_1$–$C_4$)-alkylsulfinyl-($C_1$–$C_4$)-alkyl, heterocyclyl-($C_1$–$C_4$)-alkylsulfonyl-($C_1$–$C_4$)-alkyl, heterocyclyl-($C_1$–$C_4$)-alkylamino-($C_1$–$C_4$)-alkyl, heterocyclyl-($C_1$–$C_4$)-alkylsulfonyloxy-($C_1$–$C_4$)-alkyl, heterocyclyl-($C_1$–$C_4$)-alkylsulfonylamino-($C_1$–$C_4$)-alkyl, heterocyclyl-($C_1$–$C_4$)-alkylcarbonyl-($C_1$–$C_4$)-alkyl, heterocyclyl-($C_1$–$C_4$)-alkylcarbonyloxy-($C_1$–$C_4$)-alkyl, heterocyclyl-($C_1$–$C_4$)-alkoxycarbonyl-($C_1$–$C_4$)-alkyl, heterocyclyl-($C_1$–$C_4$)-alkylcarbonylamino-($C_1$–$C_4$)-alkyl, heterocyclyl-($C_1$–$C_4$)-alkylcarbonylamino-($C_1$–$C_4$)-alkyl, heterocyclyl-($C_1$–$C_4$)-alkylaminocarbonyl-($C_1$–$C_4$)-alkyl,

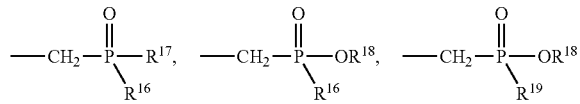

or O—$(CH_2)_p$—O—$(CH_2)_w$—$R^{20}$;

W is one of the groups $W^1$, $W^2$, $W^3$ or $W^4$

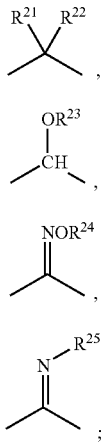

Y is O or $NR^{26}$;

E together with the two carbon atoms to which it is attached is a phenyl ring or a 5- or 6-membered heterocycle which may be saturated, partially saturated, fully unsaturated or aromatic and contains 1, 2 or 3 heteroatoms from the group consisting of oxygen, sulfur and nitrogen, where the heterocycle contains not more than 2 sulfur or 2 oxygen atoms and the phenyl ring or heterocycle which contains the group E is unsubstituted or mono- or polysubstituted by ($C_{1-6}$)-alkyl, halo-($C_1$–$C_6$)-alkyl, ($C_1$–$C_6$)-alkoxy, halo-($C_1$–$C_6$)-alkoxy,($C_1$–$C_6$)-alkylthio, halo-($C_1$–$C_6$)-alkylthio, ($C_1$–$C_6$)-alkylsulfinyl, halo-($C_1$–$C_6$)-alkylsulfinyl, ($C_1$–$C_6$)-alkylsulfonyl, halo-($C_1$–$C_6$)-alkylsulfonyl, aminosulfonyl, ($C_1$–$C_6$)-alkylaminosulfonyl, ($C_2$–$C_{12}$)-dialkylaminosulfonyl, $NR^{26}R^{27}$, ($C_2$–$C_6$)-alkoxyalkyl, ($C_2$–$C_6$)-alkoxycarbonyl, ($C_2$–$C_6$)-alkylcarbonyl, halogen, cyano, nitro or by pyridyl;

$R^1$ is halogen, cyano, nitro, $(Y)_n$—$S(O)_q$—$R^{28}$, $(Y)^n$—CO—$R^{15}$ or is ($C_1$–$C_6$)-alkyl, ($C_2$–$C_6$)-alkenyl, ($C_2$–$C_6$)-alkynyl or ($C_1$–$C_4$)-alkoxy which are substituted by V halogen atoms or K ($C_1$–$C_4$)-alkoxy groups;

$R^2$, $R^3$, $R^5$ and $R^7$ independently of one another are hydrogen or ($C_1$–$C_6$)-alkyl;

$R^4$ is hydrogen, or is ($C_1$–$C_6$)-alkyl, ($C_3$–$C_6$)-cycloalkyl, tetrahydropyran-3-yl, tetrahydropyran-4-yl or tetrahydrothiopyran-3-yl which are substituted by K radicals from the group consisting of halogen, ($C_1$–$C_6$)-alkylthio and ($C_1$–$C_6$)alkoxy;

$R^6$ is hydrogen, ($C_1$–$C_6$)-alkyl or $CO_2R^{15}$, or $R^4$ and $R^6$ together form a bond or a three- to six-membered carbocyclic ring;

$R^8$ is $OR^{29}$, thio, ($C_1$–$C_6$)-alkylthio, halo-($C_1$–$C_6$)-alkylthio, ($C_1$–$C_6$)-alkylsulfinyl, halo-($C_1$–$C_6$)-alkylsulfinyl, ($C_1$–$C_6$)-alkylsulfonyl, halo-($C_1$–$C_6$)-alkylsulfonyl, halogen, $NR^{26}R^{27}$, phenylthio, phenylsulfonyl or phenylcarbonylmethylthio, where the three last-mentioned groups are substituted by K radicals from the group consisting of ($C_1$–$C_3$)-alkyl, halogen, cyano and nitro;

$R^9$ is hydrogen, ($C_1$–$C_6$)-alkyl, halo-($C_1$–$C_6$)-alkyl, ($C_2$–$C_6$)-alkenyl, ($C_2$–$C_6$)alkynyl, $CH_2CH_2OR^{30}$ or is phenyl or benzyl which are substituted in the phenyl ring by K radicals from the group consisting of ($C_1$–$C_3$)-alkyl, halogen, cyano and nitro;

$R^{10}$ is hydrogen, ($C_1$–$C_6$)-alkyl, halo-($C_1$–$C_6$)-alkyl, ($C_1$–$C_6$)-alkoxy, halo-($C_1$–$C_6$)-alkoxy, halogen, cyano or nitro;

$R^{11}$ is hydrogen, ($C_1$–$C_6$)-alkyl, halo-($C_1$–$C_6$)-alkyl, ($C_3$–$C_6$)-cycloalkyl or halo-($C_3$–$C_6$)-cycloalkyl;

$R^{12}$ is hydrogen, ($C_2$–$C_6$)-alkoxycarbonyl, halo-($C_2$–$C_6$)-alkoxycarbonyl, $S(O)_qR^{28}$, $CO_2H$ or cyano;

$R^{13}$ is ($C_1$–$C_6$)-alkyl, halo-($C_1$–$C_6$)-alkyl, halo-($C_3$–$C_6$)-cycloalkyl or is ($C_3$–$C_6$)cycloalkyl which is substituted by a radical ($C_1$–$C_3$)-alkyl;

$R^{14}$ is cyano, ($C_2$–$C_6$)-alkoxycarbonyl, ($C_2$–$C_6$)-alkylcarbonyl, $S(O)_q$—$R^{30}$ or $C(O)NR^{26}R^{27}$;

$R^{15}$ is ($C_1$–$C_4$)-alkyl, halo-($C_1$–$C_4$)-alkyl or $NR^{26}R^{27}$;

$R^{16}$ and $R^{17}$ independently of one another are ($C_1$–$C_6$)-alkyl, ($C_2$–$C_6$)-alkenyl, ($C_2$–$C_6$)-alkynyl, halo-($C_1$–$C_6$)-alkyl, aryl or aryl-($C_1$–$C_6$)-alkyl which are substituted by K radicals from the group consisting of halogen, cyano, nitro, ($C_1$–$C_6$)-alkyl, halo-($C_1$–$C_6$)-alkyl, ($C_1$–$C_6$)-alkoxy and halo-($C_1$–$C_6$)-alkoxy;

$R^{18}$ and $R^{19}$ independently of one another are hydrogen or $R^{16}$, or $R^{18}$ and $R^{19}$ together form a ($C_2$–$C_5$)-alkenyl chain;

$R^{20}$ is ($C_1$–$C_4$)-alkyl, ($C_2$–$C_8$)-alkenyl, ($C_2$–$C_6$)-alkynyl, halo-($C_1$–$C_6$)-alkyl, halo-($C_2$–$C_6$)-alkenyl, halo-($C_2$–$C_6$)-alkynyl, ($C_1$–$C_6$)-alkoxy, ($C_2$–$C_6$)-alkenyloxy, ($C_2$–$C_6$)-alkynyloxy, halo-($C_1$–$C_6$)-alkoxy, halo-($C_2$–$C_6$)-alkynyloxy or halo-($C_2$–$C_6$)-alkenyloxy;

$R^{21}$ is hydrogen, ($C_1$–$C_4$)-alkyl, halo-($C_1$–$C_4$)-alkyl, $Z^1$, O—$Z^1$, S-$Z^1$ or $NR^{30}Z^1$;

$R^{22}$ is hydrogen, ($C_1$–$C_4$)-alkyl, ($C_2$–$C_4$)-alkenyl or ($C_2$–$C_4$)-alkynyl, or $R^{21}$, $R^{22}$ together with the carbon atom to which they are attached form a carbonyl group or an O—$CH_2CH_2$—O group which is substituted by 9 ($C_1$–$C_3$)-alkyl radicals, or $R^{21}$ is hydrogen and $R^{22}$ is $Z^1$;

$R^{23}$ and $R^{24}$ independently of one another are ($C_1$–$C_6$)-alkyl, halo-($C_1$–$C_6$)-alkyl, ($C_3$–$C_6$)-cycloalkyl, ($C_2$–$C_6$)-alkenyl, halo-($C_2$–$C_6$)-alkenyl, ($C_2$–$C_6$)-alkynyl, halo-($C_2$–$C_6$)-alkynyl or $Z^1$;

$R^{25}$ is $Z^1$;

$R^{26}$ is hydrogen or ($C_1$–$C_6$)-alkyl;

$R^{27}$ is hydrogen, ($C_1$–$C_6$)-alkyl or ($C_1$–$C_6$)-alkoxy, or $R^{26}$ and $R^{27}$ together form $(CH_2)_2$, $(CH_2)_3$, $(CH_2)_4$, $(CH_2)_5$, or $(CH_2)_2O(CH_2)_2$;

$R^{28}$ is ($C_1$–$C_4$)-alkyl, halo-($C_1$–$C_4$)-alkyl or $NR^{26}R^{27}$;

$R^{29}$ is hydrogen, ($C_1$–$C_6$)-alkyl, halo-($C_1$–$C_6$)-alkyl, ($C_2$–$C_6$)-alkoxyalkyl, formyl, ($C_2$–$C_6$)-alkylcarbonyl, ($C_2$–$C_6$)-alkoxycarbonyl, $C(O)NR^{26}R^{27}$,($C_1$–$C_6$)-alkylsulfonyl, halo-($C_1$–$C_6$)-alkylsulfonyl, or is phenyl, benzyl, benzoyl, $CH_2C(O)$phenyl or phenylsulfonyl which are substituted in the phenyl ring by K radicals from the group consisting of ($C_1$–$C_3$)-alkyl, halogen, cyano and nitro;

$R^{30}$ is $(C_1–C_6)$-alkyl or $(C_1–C_6)$-alkoxy;
a is 0, 1, 2, 3 or 4;
b is 1 or 2;
k is 0, 1, 2 or 3;
l is 0, 1 or 2;
m is 0 or 1;
n is 0 or 1;
p is 1, 2 or 3;
q is 0, 1 or 2;
v is 0, 1, 2, 3, 4 or 5,
w is 0, 1, 2 or 3, and
B) at least one compound (Component B) from one of the groups
B-a) herbicides which are selectively active in cereals against monocotyledonous and/or dicotyledonous harmful plants,
B-b) herbicides which are selectively active in corn against monocotyledonous and/or dicotyledonous harmful plants,
B-c) herbicides which are selectively active in rice against monocotyledonous and/or dicotyledonous harmful plants,
B-d) herbicides which are nonselectively active in land which is not under cultivation and/or selectively active in transgenic crops against monocotyledonous and/or dicotyledonous harmful plants, where these compositions comprise the compounds of the formula (I) or their salts (Component A) and the compounds of groups B-a) to B-d) (Component B) in a ratio by weight of from 1:2000 to 2000:1.

In formula (I) and in all subsequent formulae, carbon-containing radical chains such as alkyl, alkoxy, haloalkyl, haloalkoxy, alkylamino and alkylthio and the corresponding radicals which are unsaturated and/or substituted in the carbon skeleton, such as alkenyl and alkynyl, can in each case be straight-chain or branched. Unless specifically indicated otherwise, the lower carbon skeletons, for example having 1 to 6 C atoms or, in the case of unsaturated groups, having 2 to 4 C atoms, are preferred for these radicals. Alkyl radicals, also in the composed meanings, such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl; alkynyl is, for example, propargyl, but-2-yn-1-yl, but-3-yn-1-yl, 1-methyl-but-3-yn-1-yl. The multiple bond can be in any position of the unsaturated radical.

Unless indicated otherwise, cycloalkyl is a carbocyclic saturated ring system having three to nine C atoms, for example cyclopropyl, cyclopentyl or cyclohexyl. Analogously, cycloalkenyl is a monocyclic alkenyl group having three to nine carbon ring members, for example cyclopropenyl, cyclobutenyl, cyclopentenyl and cyclohexenyl, where the double bond can be in any position.

In the case of a disubstituted amino group, such as dialkylamino, these two substituents can be identical or different.

Halogen is fluorine, chlorine, bromine or iodine. Haloalkyl, -alkenyl and -alkynyl is alkyl, alkenyl and alkynyl, respectively, which is partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

The term "heterocyclyl" is to be understood as meaning the radicals of three- to nine-membered saturated, partially or fully unsaturated heterocycles which contain one to three heteroatoms selected from the group consisting of oxygen, nitrogen and sulfur. If chemically possible, these radicals can be attached at any position of the heterocycle. Heterocyclyl is preferably aziridinyl, oxiranyl, tetrahydrofuranyl, tetrahydropyranyl, tetrahydrothienyl, pyrrolidinyl, isoxazolidinyl, isoxazolinyl, thiazolinyl, thiazolidinyl, pyrazolidinyl, morpholinyl, piperidinyl, dioxolanyl, dioxanyl, piperazinyl, oxepanyl, azepanyl.

Heteroaryl is the radical of a heteroaromatic compound which, in addition to carbon ring members, contains one to five heteroatoms from the group consisting of nitrogen, oxygen and sulfur. Heteroaryl is preferably furanyl, thienyl, pyrrolyl, pyrazolyl, imidazolyl, oxazolyl, thiazolyl, isoxazolyl, isothiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, pyridyl, pyridazinyl, pyrimidinyl, pyrazinyl, 1,2,4-triazinyl, 1,3,5-triazinyl.

Aryl is an aromatic mono- or polycyclic hydrocarbon radical, for example phenyl, naphthyl, biphenyl and phenanthryl.

The term "partially or fully halogenated" is meant to express that some or all of the hydrogen atoms in the groups characterized in this manner can be replaced by identical or different halogen atoms as mentioned above.

If a group or a radical is polysubstituted, this is to be understood as meaning that when the different substituents are combined, the general principles of the construction of chemical compounds have to be followed, i.e. that no compounds are formed which are known to the person skilled in the art to be chemically unstable or not possible. This also applies accordingly to the attachment of individual radicals.

Depending on staic and/or electronic effects an oxo group may also be present in the tantomeric form, as enol group.

If a group or a radical is polysubstituted by other radicals, these other radicals can be identical or different.

If a group or a radical is mono- or polysubstituted without the number and the type of substituents being given in detail, this is to be understood as meaning that this group or this radical is substituted by one or more identical or different radicals selected from the group consisting of halogen, hydroxyl, cyano, nitro, formyl, carboxyl, amino, thio, $(C_1–C_6)$-alkyl, $(C_1–C_6)$-alkoxy, halo-$(C_1–C_6)$-alkyl, halo-$(C_1–C_6)$-alkoxy, $(C_2–C_6)$-alkenyl, $(C_2–C_6)$-alkynyl, $(C_2–C_6)$-alkenyloxy, $(C_2–C_6)$-alkynyloxy, $(C_3–C_6)$-cycloalkyl, $(C_3–C_6)$-cycloalkoxy, $(C_1–C_6)$-alkylthio, halo-$(C_1–C_6)$-alkylthio.

Depending on the type and the attachment of the substituents, the compounds of the formula I can be present as stereoisomers. If, for example, one or more alkenyl groups are present, diastereomers may exist. If, for example, one or more asymmetrically substituted carbon atoms are present, enantiomers and diastereomers may exist. From the mixtures produced in the preparation, stereoisomers can be obtained by customary separation methods, for example by chromatographic separation procedures. Stereoisomers can also be prepared selectively by using stereoselective reactions and employing optically active starting materials and/ or auxiliaries. The invention also relates to all stereoisomers and mixtures thereof which are embraced by the formula I but not defined specifically.

Of more interest are herbicidal compositions which comprise as Component A) a compound of the formula (I) in which Q is one of the radicals $Q^1$, $Q^2$, $Q^3$ or $Q^4$.

Of particular interest are herbicidal compositions which comprise as Component A) a compound of the formula (I) in which Q is one of the radicals $Q^1$, $Q^2$ or $Q^3$, preferably $Q^1$ or $Q^3$.

Of particular interest are likewise herbicidal compositions which comprise as Component A) a compound of the formula (I), in which X is a radical $X^1$.

From the group B-a), the herbicides amidosulfuron, bentazone, bromoxynil, carfentrazone-ethyl, chlortoluron, clodinafop, cloransulam-methyl, diclofop-methyl, fenoxaprop-P-ethyl, florasulam, flufenacet, fluoroglycofen-ethyl, flupyrsulfuronmethyl-sodium, iodosulfuron, isoproturon, metsulfuron, pendimethalin, pyraflufenethyl, sulfosulfuron, thifensulfuron, tralkoxydim, tribenuron, the herbicide 2-amino-4-(1-fluoro-1-methylethyl)-6-(3-phenyl-1-cyclobutyl-1-propylamino)-1,3,5-triazine known from WO 97/08156 and the herbicide N-[(4,6-dimethoxy-pyrimidin-2-yl)-aminocarbonyl]-2-methoxycarbonyl-5-methylsulfonylaminomethylbenzenesulfonamid known from WO 95/10507 are particularly suitable for controlling monocotyledonous and/or dicotyledonous harmful plants in cereals.

Very particularly suitable are bromoxynil, clodinafop, fenoxaprop-P-ethyl, iodosulfuron, pyraflufen-ethyl, tralkoxydim, 2-amino-4-(1-fluoro-1-methylethyl)-6-(3-phenyl-1-cyclobutyl-1-propylamino)-1,3,5-triazine and sulfonyl ureas of the formula (II).

From the group B-b), the herbicides acetochlor, alachlor, atrazine, bromoxynil, carfentrazone-ethyl, dicamba, diflufenzopyr, dimethenamid, flufenacet, flumetsulam, fluthiacet-methyl, halosulfuron, imazamox, imazapyr, imazaquin, imazethapyr, idosulfuron, metolachlor, metosulam, metribuzin, nicosulfuron, pethoxamid, pendimethalin, primisulfuron, prosulfuron, pyridate, rimsulfuron, thenylchlor, thifensulfuron-methyl, tritosulfuron and N-[4,6-dimethoxypyrimidin-2-yl)-aminocarbonyl]-2-dimethylaminocarbonyl-5-formylaminobenzenesulfonamide are particularly suitably for controlling monocotyledonous and/or dicotyledonous harmful plants in corn.

Very particularly suitable are bromoxynil, dicamba, diflufenzopyr, iodosulfuron, nicosulfuron, rimsulfuron and N-[(4,6-dimethoxypyrimidin-2-yl)-aminocarbonyl]-2-dimethylaminocarbonyl-5-formylaminobenzenesulfonamide.

From the group B-c) the herbicides anilofos, azimsulfuron, benfuresate, bensulfuron, bentazone, benthiocarb, bromobutide, bispyribac-sodium, butachlor, cinosulfuron, clomazone, cyclosulfamuron, ethoxysulfuron, esprocarb, imazosulfuron, KPP-314, pyribenzoxim, mefenacet, molinate, oxaziclomefone, OK9701, oxadiargyl, pretilachlor, propanil, pyrazosulfuron, quinclorac, thenylchlor, triclopyr and the herbicide 1-(3-chloro-4,5,6,7-tetrahydropyrazolo-[1,5-a]-pyrid-2-yl)-5-(methylpropargylamino)-4-pyrazolylcarbonitrile known from EP-A 0 863 705 are particularly suitable for controlling monocotyledonous and/or dicotyledonous harmful plants in rice.

Very particularly suitable are benfuresate, bensulfuron, ethoxysulfuron, molinate, oxaziclomefone and 1-(3-chloro-4,5,6,7-tetrahydropyrazolo-[1,5-a]-pyrid-2-yl)-5-(methylpropargylamino)-4-pyrazolylcarbonitrile.

From the group B-d), the herbicides glufosinate, glyphosate, imazamox, imazapyr, imazaquin, imazethapyr and sulfosate are particularly suitable for controlling monocotyledonous and/or dicotyledonous harmful plants on land which is not under cultivation and/or selectively in transgenic crops. Very particularly suitable are glufosinate and glyphosate.

The active compounds mentioned above by their common names are known, for example, from "The Pesticide Manual", 11th edition, 1997, British Crop Protection Council, and/or are shown in the table below:

| Common name or Code No. | Structure |
|---|---|
| florasulam | 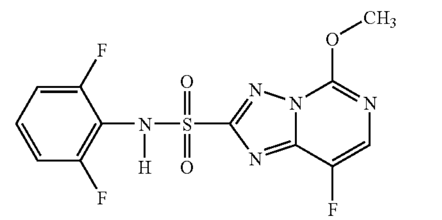 |
| flufenacet | 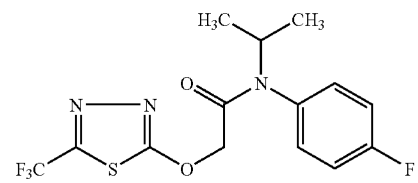 |
| iodosulfuron | 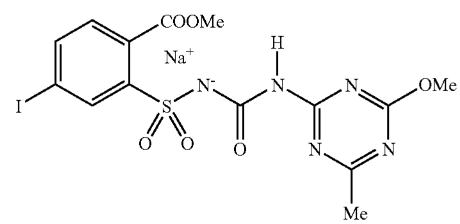 |
| oxaziclomefone (MY 100) | 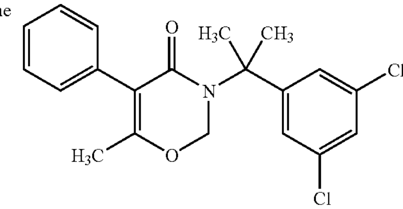 |
| pethoxamid | 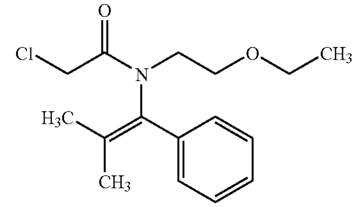 |

-continued

| Common name or Code No. | Structure |
|---|---|
| pyribenzoxim (LGC40863) | 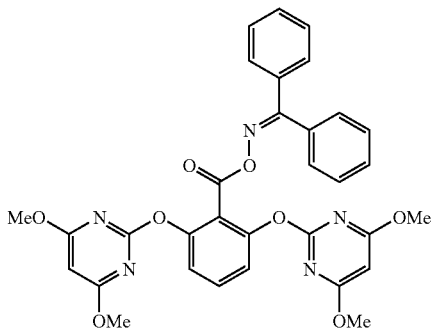 |
| tritosulfuron | 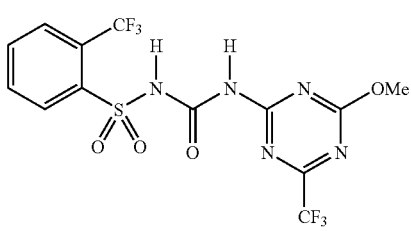 |

In the combinations according to the invention, application rates in the range from 1 to 2000 g, preferably from 10 to 500 g, of active ingredient per hectare (ai/ha) of the Component A) and from 1 to 2000 g, preferably from 1 to 500 g of the Component B) are generally required.

The weight ratios of the Components A) to B) to be used can be varied within wide ranges. The ratio is preferably in the range from 1:50 to 500:1, in particular in the range from 1:20 to 50:1. Optimum weight ratios may depend on the particular field of application, on the weed spectrum and the active compound combination used and can be determined in preliminary experiments.

The compositions according to the invention can be employed for the selective control of annual and perennial monocotyledonous and dicotyledonous harmful plants in crops of cereals (for example barley, oats, rye, wheat), corn and rice and in crops of transgenic useful plants or crops of useful plants selected by classical means which are resistant to active compounds A) and B). Likewise, they can be employed for controlling undesirable harmful plants in plantation crops such as oil palm, coconut palm, Indian-rubber tree, citrus, pineapples, cotton, coffee, coca and the like, and also in fruit production and viticulture.

The compositions according to the invention act against a broad spectrum of weeds. They are suitable, for example, for controlling annual and perennial harmful plants such as, for example, from the species *abutilon, alopecurus, avena, chenopodium, cynoden, cyperus, digitaria, echinochloa, elymus, galium, ipomoea, lamium, matricaria, scirpus, setaria, sorghum, veronica, viola* and *xanthium*.

The herbicidal compositions according to the invention are also distinguished by the fact that the effective dosages of the Components A) and B) used in the combinations are reduced with respect to an individual dosage, so that it is possible to reduce the required active compound application rates.

The invention also provides a method for controlling undesirable vegetation, which method comprises applying one or more herbicides A) together with one or more herbicides B) to the harmful plants, parts thereof or to the area under cultivation.

When herbicides of Type A) and B) are applied jointly, superadditive (=synergistic) effects are observed. The activity in the combinations is more pronounced than the expected sum of the activities of the individual herbicides employed and the activity of the particular individual herbicide A) and B). The synergistic effects permit the application rate to be reduced, a broader spectrum of broad-leaved weeds and weed grasses to be controlled, more rapid onset of the herbicidal action, a more prolonged action, better control of the harmful plants by only one application, or few applications, and widening of the period of time within which the product can be used. These properties are required in weed control practice to keep agricultural crops free from undesirable competing plants and thus to ensure and/or to increase quality and quantity of the yields. These novel combinations markedly surpass the prior art with respect to the described properties.

The active compound combinations according to the invention can either be present as mixed formulations of the Components A) and B), if appropriate together with other customary formulation auxiliaries, which mixed formulations are then applied in the usual manner in the form of a dilution with water, or else they can be prepared in the form of so-called tank mixes by joint dilution with water of the components which are formulated separately, or partly separately.

The Components A) and B) can be formulated in various ways, depending on the prevailing biological and/or physicochemical parameters. Suitable general possibilities for formulations are, for example: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed dressing products, granules for soil application or for broadcasting or water-dispersible granules (WG), ULV formulations, microcapsules or waxes.

The individual types of formulation are known in principle and are described, for example, in: Winnacker-Küchler, "Chemische Technologie" [Chemical Technology], Vol. 7, C. Hauser Verlag Munich, 4th Ed. 1986; van Valkenburg, "Pesticides Formulations", Marcel Dekker N.Y., 1973; K. Martens, "Spray Drying Handbook", 3rd Ed. 1979, G. Goodwin Ltd. London. The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler, "Chemische Technologie" [Chemical Technology], Vol. 7, C. Hauser Verlag Munich, 4th Ed. 1986.

Based on these formulations, it is also possible to prepare combinations with other pesticidally active substances, such as other herbicides, fungicides or insecticides, and also safeners, fertilizers and/or growth regulators, for example in the form of a ready mix or tank mix.

Wettable powders are preparations which are uniformly dispersible in water and which, besides the active compound, also comprise ionic or nonionic surfactants (wetting agents, dispersants), for example polyethoxylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or an inert substance.

Emulsifiable concentrates are prepared by dissolving the active compound in an organic solvent, for example butanol, cyclohexanone, dimethylformamide, xylene or else higher-boiling aromatics or hydrocarbons, with the addition of one or more ionic or nonionic surfactants (emulsifiers). Examples of emulsifiers which can be used are: calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained by grinding the active compound with finely divided solid materials, for example talc, natural clays, such as kaolin, bentonite and pyrophyllite, or diatomaceous earth.

Granules can be prepared either by spraying the active compound onto absorptive, granulated inert material, or by applying active compound concentrates to the surface of carriers, such as sand, kaolinite or granulated inert material, with the aid of binders, for example polyvinyl alcohol, sodium polyacrylate or else mineral oils. Suitable active compounds can also be granulated in the manner customary for the preparation of fertilizer granules, if desired as a mixture with fertilizers. Water-dispersible granules are, in general, prepared by processes such as spray-drying, fluidized-bed granulation, disk granulation, mixing using high-speed mixers, and extrusion without solid inert material.

The agrochemical preparations generally comprise from 0.1 to 99 percent by weight, in particular from 0.2 to 95% by weight, of active compounds of types A) and B), the following concentrations being customary, depending on the type of formulation: In wettable powders, the active compound concentration is, for example, approximately 10 to 95% by weight, the remainder to 100% by weight being composed of customary formulation components. In the case of emulsifiable concentrates, the active compound concentration can be, for example, from 5 to 80% by weight. Formulations in the form of dusts in most cases comprise from 5 to 20% by weight of active compound, sprayable solutions approximately 0.2 to 25% by weight of active compound. In the case of granules, such as dispersible granules, the active compound content depends partly on whether the active compound is in liquid or solid form and on which granulation auxiliaries and fillers are used. In general, the content in the water-dispersible granules amounts to between 10 and 90% by weight. In addition, the active compound formulations mentioned comprise, if appropriate, the tackifiers, wetting agents, dispersants, emulsifiers, preservatives, antifreeze agents, solvents, fillers, colorants, carriers, antifoams, evaporation inhibitors and pH or viscosity regulators which are customary in each case.

For use, the formulations, which are in commercially available form, are, if appropriate, diluted in a customary manner, for example using water in the case of wettable powders, emulsifiable concentrates, dispersions and water-dispersible granules. Preparations in the form of dusts, soil granules, granules for spreading and sprayable solutions, are conventionally not diluted any further with other inert substances prior to use.

The active compounds can be applied to the plants, parts of the plants, seeds of the plants or the area under cultivation (tilled soil), preferably to the green plants and parts of the plants and, if desired, additionally to the tilled soil.

A possible use is the joint application of the active compounds in the form of tank mixes, where the concentrated formulations of the individual active substances, in the form of their optimal formulations, are mixed jointly with water in the tank, and the spray mixture obtained is applied.

A joint herbicidal formulation of the combination according to the invention of the components A) and B) has the advantage that it can be applied more easily because the amounts of the components have already been adjusted with respect to one another to the correct ratio. Moreover, the auxiliaries of the formulation can be selected to suit each other in the best possible way, while a tank mix of various formulations may result in undesirable combinations of auxiliaries.

A. FORMULATION EXAMPLES a) A dust (WP) is obtained by mixing 10 parts by weight of an active compound/active compound mixture and 90 parts by weight of talc as inert substance and comminuting the mixture in a hammer mill.

b) A wettable powder (WG) which is readily dispersible in water is obtained by mixing 25 parts by weight of an active compound/active compound mixture, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (Triton X 207), 3 parts by weight of isotridecanol polyglycol ether (8 EO) and 71 parts by weight of paraffinic mineral oil (boiling range for example approximately 255 to 277° C.) and grinding the mixture in a ball mill to a fineness of below 5 microns.

d) An emulsifiable concentrate (EC) is obtained from 15 parts by weight of an active compound/active compound mixture, 75 parts by weight of cyclohexanone as solvent and 10 parts by weight of ethoxylated nonylphenol as emulsifier.

e) Water-dispersible granules are obtained by mixing
- 75 parts by weight of an active compound/active compound mixture,
- 10 parts by weight of calcium lignosulfonate,
- 5 parts by weight of sodium lauryl sulfate,
- 3 parts by weight of polyvinyl alcohol and
- 7 parts by weight of kaolin
- grinding the mixture in a pinned-disk mill and granulating the powder in a fluidized bed by spraying on water as granulation liquid.

f) Water-dispersible granules are also obtained by homogenizing and precomminuting, in a colloid mill,
- 25 parts by weight of an active compound/active compound mixture,
- 5 parts by weight of sodium 2,2'-dinaphthylmethane-6,6'-disulfonate,
- 2 parts by weight of sodium oleoylmethyltaurinate,
- 1 part by weight of polyvinyl alcohol,
- 17 parts by weight of calcium carbonate and
- 50 parts by weight of water,
- subsequently grinding the mixture in a bead mill and atomizing and drying the resulting suspension in a spray tower by means of a single-substance nozzle.

B. BIOLOGICAL EXAMPLES

Outdoors, crop plants were grown on plots of a size of from 5 to 10 m$^2$ on various soils and under various climatic conditions, and the natural presence of harmful plants and/or their seeds in the soil was utilized for the experiments. The treatment with the compositions according to the invention or the herbicides A) and B) applied individually was carried out after emergence of the harmful and the crop plants, in general at the 2- to 4-leaf stage. The active compounds or active compound combinations, formulated as WG, WP or EC, was carried out by the post-emergence method. After 2 to 8 weeks, visual evaluation was carried out in comparison with an untreated comparative group. It was found that the compositions according to the invention have synergistic herbicidal action against economically important mono- and dicotyledonous harmful plants, i.e. that most of the compositions according to the invention have higher, some considerably higher, herbicidal activity than the sum of the activities of the individual herbicides. In addition, the herbicidal activities of the compositions according to the invention exceed the expected values according to Colby. In contrast, the treatment caused insignificant, if any, damage to the crop plants.

If the observed activity values of the mixtures already exceed the formal sum of the values for the trials with individual applications, they also exceed the expected value according to Colby which is calculated using the following formula (cf. S. R. Colby; in Weeds 15 (1967) pp. 20 to 22):

$$E = \frac{A + B}{A \times B} \times 100$$

The figures denote:
A, B=Activity of Components A and B in percent, at a dosage of a and b gram of ai/ha, respectively.
E=Expected value in % at a dosage of a+b gram of ai/ha.

The values observed in the experimental examples below exceed the expected values according Colby.

The abbreviations denote:

Harmful Plants

| CHEAL | Chenopodium album | ECHCG | Echinocloa crus galli |
|---|---|---|---|
| GALAP | Galium aparine | KCHSC | Kochia scoparia |
| LAMAM | Lamium amplexicaule | HBPU | Pharbitis purpurea |
| POLCO | Polygonum convolvulus | POROL | Portulaca oleracea |

Crop Plants

| | HORVS | Hordeum vulgaris |
|---|---|---|
| | TRZDU | Triticum davam |
| | ZEMX | Zea mays |

The following compounds were used in the examples:

A1
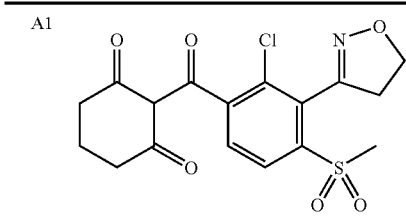

A2
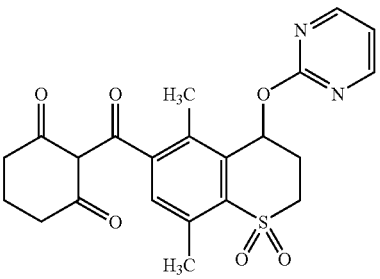

A3
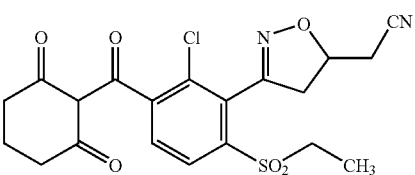

A4
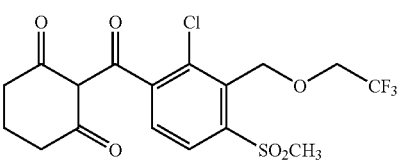

B1
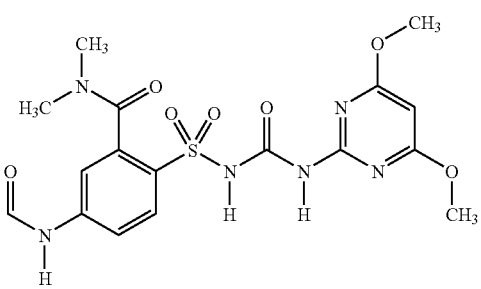

B2  glufosinate

B3
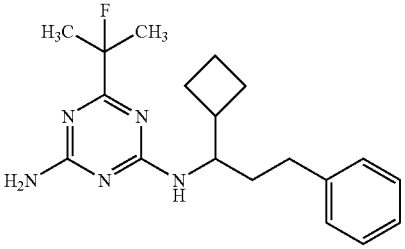

B4  iodosulfuron
B5  bromoxynil

Example B.I

| Compound | Dosage [g of ai/ha] | KCHSC | |
|---|---|---|---|
| | | found | value E (according to Colby) |
| A1 | 25 | 28 | |
| B1 | 30 | 30 | |
| | 60 | 33 | |

-continued

|  | | KCHSC | |
|---|---|---|---|
| Compound | Dosage [g of ai/ha] | found | value E (according to Colby) |
| A1 + B1 | 25 + 30 | 65 | 50 |
|  | 25 + 60 | 72 | 52 |

Example B.II

|  | | PHBPU | |
|---|---|---|---|
| Compound | Dosage [g of ai/ha] | found | value E (according to Colby) |
| A2 | 50 | 65 |  |
| B1 | 30 | 20 |  |
| A2 + B1 | 50 + 30 | 90 | 52 |

Example B.III

|  | | PHBPU | |
|---|---|---|---|
| Compound | Dosage [g of ai/ha] | found | value E (according to Colby) |
| A2 | 100 | 45 |  |
| B2 | 500 | 43 |  |
| A2 + B2 | 100 + 500 | 94 | 67 |

Example B.IV

|  | | CHEAL | |
|---|---|---|---|
| Compound | Dosage [g of ai/ha] | found | value E (according to Colby) |
| A2 | 100 | 34 |  |
| B2 | 500 | 60 |  |
| A2 + B2 | 100 + 500 | 100 | 74 |

Example B.V

|  | | POROL | |
|---|---|---|---|
| Compound | Dosage [g of ai/ha] | found | value E (according to Colby) |
| A2 | 100 | 0 |  |
| B1 | 30 | 43 |  |
| A2 + B1 | 100 + 30 | 80 | 43 |

Example B.VI

|  | | CHEAL | | |
|---|---|---|---|---|
| Compound | Dosage [g of ai/ha] | found | value E (according to Colby) | HORVS found |
| A3 | 75 | 0 |  | 0 |
| B3 | 100 | 30 |  | 0 |
| A3 + B3 | 75 + 100 | 100 | 30 | 0 |

Example B.VII

|  | | BRAPL | | |
|---|---|---|---|---|
| Compound | Dosage [g of ai/ha] | found | value E (according to Colby) | ZEAMX found |
| A3 | 75 | 65 |  | 0 |
| B5 | 300 | 0 |  | 0 |
| A3 + B5 | 75 + 300 | 80 | 65 | 0 |

Example B.VIII

|  | | POROL | | |
|---|---|---|---|---|
| Compound | Dosage [g of ai/ha] | found | value E (according to Colby) | TRZDU found |
| A4 | 25 | 5 |  | 5 |
| B4 | 2.5 | 20 |  | 15 |
| A4 + B4 | 25 + 2.5 | 60 | 24 | 15 |

What is claimed is:

1. The herbicidal composition comprising an effective amount of Compound A):

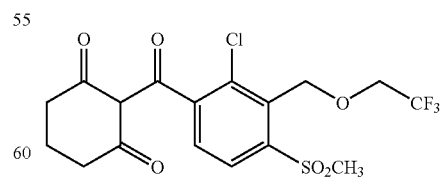

and

Compound B) nicosulfuron.

* * * * *